United States Patent [19]

Rotering et al.

[11] Patent Number: 5,324,511
[45] Date of Patent: * Jun. 28, 1994

[54] VACCINES AND IMMUNOGLOBULIN G-CONTAINING PREPARATIONS ACTIVE AGAINST PSEUDOMONAS AERUGINOSA

[75] Inventors: Heinz Rotering, Rödermark-Waldacker, Fed. Rep. of Germany; Johann Eibl; Friedrich Dorner, both of Vienna, Austria

[73] Assignee: Immuno Aktiengesellschaft, Vienna, Austria

[*] Notice: The portion of the term of this patent subsequent to Aug. 7, 2007 has been disclaimed.

[21] Appl. No.: 363,144

[22] Filed: Jun. 8, 1989

[30] Foreign Application Priority Data

Aug. 29, 1988 [AT] Austria ................... 2113/88

[51] Int. Cl.$^5$ ............. A61K 39/40; A61K 39/104; A61K 39/02; G07K 3/12
[52] U.S. Cl. ..................... 424/87; 530/350; 424/92; 424/93 N
[58] Field of Search ............ 424/87, 88, 92, 93 P, 424/93 N; 530/350

[56] References Cited

U.S. PATENT DOCUMENTS

| | | | |
|---|---|---|---|
| 4,831,121 | 5/1989 | Montie | 530/350 |
| 4,946,677 | 4/1990 | Dorner | 424/92 |

OTHER PUBLICATIONS

Holder et al. J. of I 33:276–280 1982.
Holder et al. J. Trauma (abs) 1986 26:118–22.
Montie et al. J. of Clin Micro 18:452–456 1983.
Warren et al. Ann Rev Imm 4:369–88 1986 369 & 371.
Holder et al. J of I 35:276–280 1982.
Montie et al., "Loss of Virulence Associated with Absence of Flagellum in an Isogenic Mutant of Pseudomonas Aeruginosa in the Burned-Mouse Model", pp. 1296–1298, 1982.
Holder et al., "Flagellar Preparation from Pseudomonas Aeruginosa: Animal Protection Studies", pp. 276–280, 1982.
Montie et al., "Electrophoretic Separation and Molecular Weight Characterization of Pseudomonas Aeruginosa H-Antigen Flagellins", pp. 770–774, 1985.

Primary Examiner—Christine M. Nucker
Assistant Examiner—Hazel F. Sulberry
Attorney, Agent, or Firm—Foley & Lardner

[57] ABSTRACT

Vaccines that are active against Pseudomonas aeruginosa infections contain a single flagellar (H) antigen of serotype a or a combination of a single flagellar (H) antigen of serotype a with a flagellar (H) antigen of serotype b. Applied to man, the vaccines according to the invention induce the formation of antibodies that are directed against any combination of partial flagellar (H) antigens $a_0$, $a_1$, $a_2$, $a_3$, $a_4$ and b, inhibiting the motility of Pseudomonas aeruginosa pathogens and inducing the killing of the pathogens by phagocytizing cells of the human immune system.

15 Claims, 1 Drawing Sheet

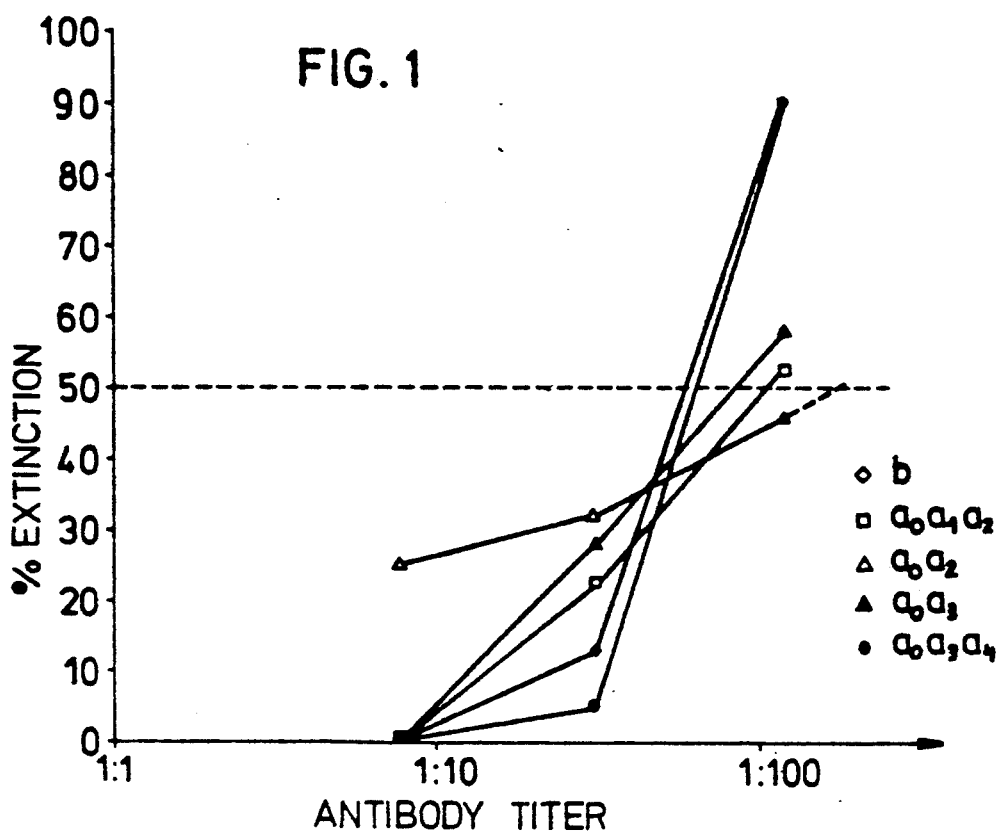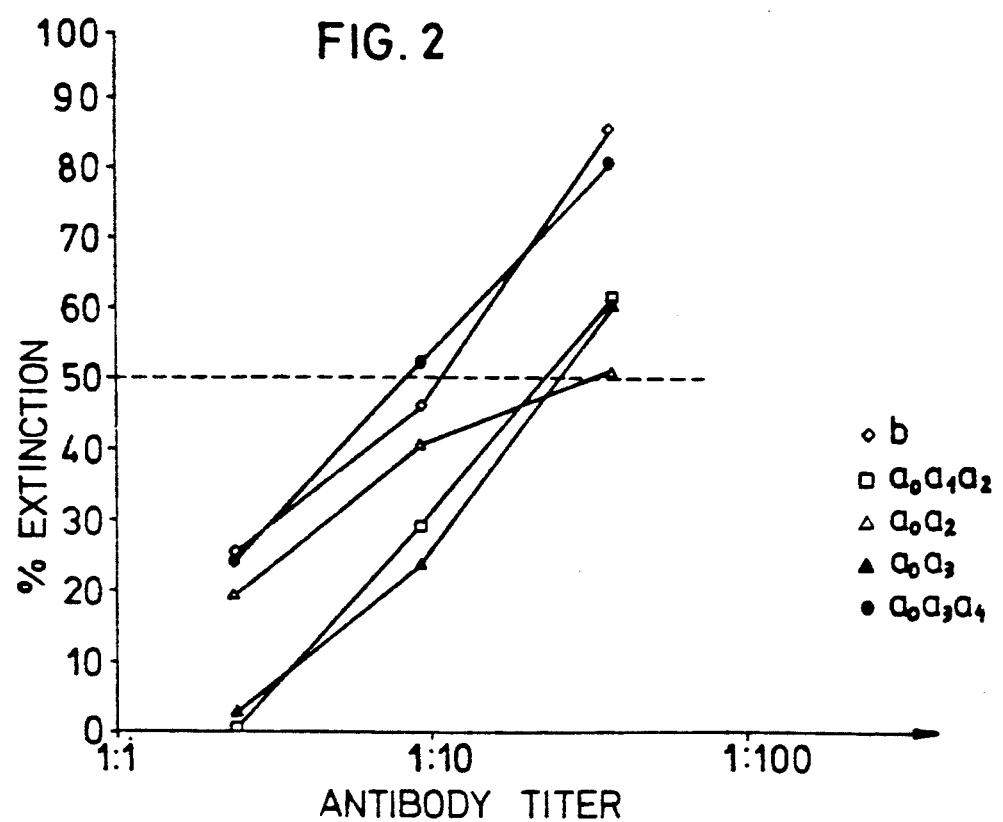

VACCINES AND IMMUNOGLOBULIN G-CONTAINING PREPARATIONS ACTIVE AGAINST PSEUDOMONAS AERUGINOSA

BRIEF SUMMARY OF THE INVENTION

The invention relates to preparations active against Pseudomonas aeruginosa infections, in particular vaccines, whose efficacy is directed against any combination of the partial flagellar (H) antigens $a_0$, $a_1$, $a_2$, $a_3$, $a_4$ and b and which are intended for active immunization, as well as to immunoglobulin G-containing preparations active against bacterium Pseudomonas aeruginosa and intended for passive protection.

BACKGROUND OF THE INVENTION

The bacterium Pseudomonas aeruginosa is an opportunistic pathogenic organism which often occurs with hospital infections, mainly in patients having an impaired immune defense, such as patients suffering from burns, persons suffering from cystic fibrosis or having organic malfunctions, and in tumor patients. Due to the occurrence of resistances, antibiotics are active against Pseudomonas infections only to a limited extent and, therefore, it has been endeavored to find immunologic methods for fighting infections caused by Pseudomonas aeruginosa.

Infections may be triggered by a variety of strains that may be characterized by O-antigens (lipopolysaccharide) and H-antigens (flagella), H- and O-antigen types being freely combinable.

It is known that the motility of Pseudomonas aeruginosa attributes to the virulence of the pathogen (Montie et al., Infect. Immunity 38, 1296–1298, 1982). Motile Pseudomonas aeruginosa strains possess a single flagellum. Burned mouse model assays have revealed that a larger percentage of mice survive if non-motile Pseudomonas aeruginosa strains are inoculated in experimentally produced burns than do if motile strains are used (Montie et al., see above). Further assays on the pathogenesis of Pseudomonas aeruginosa demonstrated that animals that had been immunized with flaggelar antigen preparations were protected when setting a burn and infecting with motile bacteria strains (Holder et al., Infect. Immunity 35, 276–280, 1982).

Pseudomonas aeruginosa flagella were investigated by serological methods, and it was demonstrated that there may be differentiated between two main types of antigens denoted as type a and type b according to R. Ansorg (Zbl. Bakt. Hyg. I. Abt. Orig. A, 242, 228–238, 1978).

In flagellar (H) antigen type a, the partial antigens $a_0$, $a_1$, $a_2$, $a_3$ and $a_4$ are differentiable by using the indirect immunofluorescence technique; they are expressed by the Pseudomonas aeruginosa strains in different combinations, the partial antigen $a_0$ being found on all flagella of type a. Flagellar (H) antigen type b behaves serologically uniformly, i.e., no subgroups can be identified.

According to Ansorg, a total of 17 H-types may be differentiated with Pseudomonas aeruginosa, i.e., one H-type b and 16 H-types of flagellar antigen a, consisting of the partial antigen $a_0$ present in all a-types and optionally of the partial antigens $a_1$ and/or $a_2$ and/or $a_3$ and/or $a_4$. Comprehensive studies of flagella of the Pseudomonas aeruginosa strains 5142 and 13030, which had been characterized by Ansorg as exclusively belonging to subgroup $a_0$, proved the same to be biochemically and immunologically identical with flagella type b (Montie et al., Infect. Immunity 49(3), 770–774 (1985)).

The obtention of polydisperse native flagellar (H) antigens (FAgs) is described in PCT publication WO 86/03974. Bacterial cultures are grown in minimal medium and subsequently are treated with a detergent, whereupon FAgs are separated from the culture. Prior to the treatment with a detergent, the bacterial culture is disintegrated and subjected to a shearing process. By the addition of detergent, the separability of the antigen from the bacteria mass is promoted; the antigens then being in suspension can be separated from the cells by differential centrifugation.

Subsequently, the antigens separated from the bacterial mass as described above can be freed from adhering impurities, such as lipopolysaccharides, nucleic acids, salts, polysaccharides and the like by chromatographic purification. The detergent still present can be eliminated by an additional column-chromatographic purification step.

The strains used for preparing Pseudomonas aeruginosa bacterial cultures and the antigens produced are listed in the following Table.

| Strain | H-type |
| --- | --- |
| M-2 | b |
| 5142 | $a_0$ (b) |
| 5940 | $a_0a_2$ |
| WR-5 | $a_0a_2$ |
| 5939 | $a_0a_3$ |
| 1210 | $a_0a_1a_2$ |
| 170018 | $a_0a_3a_4$ |

From EP-A-0 252 064 it may be taken that all individual flagellar antigens of the types described in PCT publication WO 86/03974, as components of a vaccine, exhibit protective action and that the serum obtained from mice that had been actively immunized with the flagellar antigens indicated in PCT publication WO 86/03974 is suited for the passive immunization of mice.

However, the protective effect of the individual antigens and of the antibodies derived therefrom was detectable only in the animal model and only in the homologous system, i.e., an activity was observed only against pathogens of that flagellar serotype which had been utilized for immunization.

On the physicians' part, there is the desire to have available a Pseudomonas aeruginosa vaccine whose efficacy is directed against any combination of the partial flagellar (H) antigens $a_0$, $a_1$, $a_2$, $a_3$, $a_4$ and b, since an analysis of 300 clinical Pseudomonas aeruginosa isolates by the H-antigen serotyping scheme proposed by Ansorg (Zbl. Bakt. Hyg. I. Abt. Orig. A242, 228–238, 1978) revealed that partial antigens of types a and/or b were actually detected in 98% of all motile Pseudomonas pathogens.

According to the findings disclosed in EP-A-0 252 064, a vaccine of this kind must necessarily contain all these partial antigens, i.e., must be a polyvalent vaccine.

BRIEF DESCRIPTION OF THE DRAWINGS

FIG. 1 is a graph showing the extinction rate, based on a phagocytosis test, plotted against three concentrations of several Pseudomonas immunoglobulin preparations.

FIG. 2 is a graph showing the extinction rate plotted against the antibody titers for the individual components b and $a_0a_3$ at three different concentrations.

DETAILED DESCRIPTION OF THE INVENTION

It is the object of the present invention to provide for monovalent or bivalent vaccines containing but one or two antigens, which, in man, lead to the formation of antibodies that are active against motile *Pseudomonas aeruginosa* pathogens of any combination of the partial flagellar (H) antigens $a_0$ to $a_4$ and b and, thus, against all clinically relevant serotypes, inhibiting the motility and the further propagation and reproduction of the pathogens and inducing their killing by the human immune system.

Furthermore, it is the object of the present invention to provide preparations that contain antibodies directed against these antigens and may be used for passive immunization against *Pseudomonas aeruginosa* infections.

According to the invention, this object is achieved in that the vaccines contain one single flagellar (H) antigen of serotype a or in that they contain a combination of a single flagellar (H) antigen of serotype a with flagellar (H) antigen of serotype b.

Preferably, the vaccines of the inventions are of a bivalent structure, containing both a single flagellar (H) antigen of serotype a and a flagellar (H) antigen of serotype b.

It has proved that the immunoglobulins formed upon administration of the vaccines according to the invention are capable of binding to at least 95% of all clinically relevant strains of *Pseudomonas aeruginosa* and inhibiting their motility. This binding of antibodies, in addition, leads to an opsonization and killing of the motile pathogens by the phagocytizing cells of the human immune system.

Representatives of the vaccines according to the invention may contain:

one single flagellar (H) antigen of serotype $a_0a_2$, which antigen consists of monomeric components and contains the amino acids: aspartic acid, threonine, serine, glutamic acid, glycine, alanine, valine, isoleucine, leucine, tyrosine, phenylalanine, lysine and arginine at a ratio of 68:41:37:46:44:73:29:29:37:3:10:16:16, having a molecular weight of 45,900;

or one single flagellar (H) antigen of serotype $a_0a_1a_2$, which antigen consists of monomeric components and contains the amino acids: aspartic acid, threonine, serine, glutamic acid, glycine, alanine, valine, isoleucine, leucine, tyrosine, phenylalanine, lysine and arginine at a ratio of 76:44:40:52:50:81:32:32:41:4:12:20:18, having a molecular weight of 51,250;

or a single flagellar (H) antigen of serotype $a_0a_3$, which antigen consists of monomeric components and contains the amino acids: aspartic acid, threonine, serine, glutamic acid, glycine, alanine, valine, isoleucine, leucine, tyrosine, phenylalanine, lysine and arginine at a ratio of 69:35:38:44:47:73:30:30:60:3:12:21:16, having a molecular weight of 46,700;

or a single flagellar (H) antigen of serotype $a_0a_3a_4$, which antigen consists of monomeric components and contains the amino acids: aspartic acid, threonine, serine, glutamic acid, glycine, alanine, valine, isoleucine, leucine, tyrosine, phenylalanine, lysine and arginine at a ratio of 64:33:35:42:44:68:29:29:37:3:10:19:15, having a molecular weight of 43,500.

According to a preferred embodiment, the vaccines according to the invention mentioned above additionally contain the flagellar (H) antigen of serotype b, which antigen consists of monomeric components and contains the amino acids: aspartic acid, threonine, serine, glutamic acid, glycine, alanine, valine, isoleucine, leucine, tyrosine, phenylalanine, lysine and arginine at a ratio of 74:48:48:49:51:91:38:30:43:4:13:18:18, having a molecular weight of 53,050.

The vaccines according to the invention are produced by sterile-filtering the purified flagellar (H) antigen(s) obtained from *Pseudomonas aeruginosa* cultures, optionally mixing with an adjuvant, such as Al(OH)$_3$, if desired, adding a preservant, such as merthiolate, and formulating to a galenic preparation.

The immunoglobulin G-containing preparations according to the invention, which are active against *Pseudomonas aeruginosa* infections, are produced by treating with protein precipitating agents, such as ammonium sulfate, plasma of human donors immunized with the respective flagellar (H) antigen(s), dissolving the immunoglobulin G-containing fraction precipitated, purifying the same and formulating it to a galenic preparation.

The invention will be explained in more detail by the following examples. Examples 1 and 2 illustrates the production of vaccines and example 3 illustrates the production of immunoglobulin G-containing preparations.

EXAMPLE 1

Vaccine formulation for a monovalent *Pseudomonas aeruginosa* flagella vaccine

A flagella solution obtained from a bacterium *Pseudomonas aeruginosa* 5940 culture and purified by treatment with a detergent, shearing and chromatographic treatment as described above was adjusted to a protein concentration of 100 myg/ml with distilled pyrogen-free water and was made isotonic by the addition of solid sodium chloride and merthiolate (final concentration 0.9% NaCl and 0.01% merthiolate). Subsequently, the solution was sterile filtered through 0.2 mym sterile filters.

After protein determination of the sterile filtered sample, the flagella suspension was adjusted to 25 myg/ml protein with a sterile NaCl/merthiolate solution (0.9%/0.01%) and subsequently was diluted to 20 myg/ml protein by the addition of a 1% aluminum hydroxide solution in a sterile NaCl/merthiolate solution.

The vaccine completed with adjuvant contained per ml:

20 myg flagella protein serotype $a_0a_2$
2 mg aluminum hydroxide
9 mg NaCl
0.1 mg merthiolate as stabilizer.

Further monovalent vaccines are producible in an analogous manner with the *Pseudomonas aeruginosa* strains 1210 (serotype $a_0a_1a_2$), 5939 (serotype $a_0a_3$) and 170018 (serotype $a_0a_3a_4$).

EXAMPLE 2

Vaccine formulation for a bivalent *Pseudomonas aeruginosa* flagella vaccine

Flagella suspensions obtained from cultures of bacteria strains M-2 and 5939 and purified by detergent treatment and gel filtration as described above were adjusted to a concentration of 100 myg/ml protein with distilled pyrogen-free water and were made isotonic by the addition of solid sodium chloride and merthiolate (final concentration 0.9% NaCl and 0.01% merthiolate). Subsequently, the solutions were sterile filtered through 0.2 mym filters.

After protein determination of the sterile filtered samples, the flagella suspensions were diluted with sterile NaCl/merthiolate solution (0.9%/0.01%), the M-2 flagella suspension being adjusted to 50 myg/ml and the 5939 flagella suspension being adjusted to 25 myg/ml. The two suspensions were united at equal volumina and were adjusted to antigen concentrations of 20 and 10 myg/ml, respectively, by the addition of 1% aluminum hydroxide solution in sterile NaCl/merthiolate solution.

The vaccine completed with adjuvant contained per ml:

20 myg flagella protein serotype b
10 myg flagella protein serotype $a_0a_3$
2 mg aluminum hydroxide
9 mg NaCl
0.1 mg merthiolate as stabilizer.

Instead of the suspension of flagella of the Pseudomonas strain 5939 described above, flagella of serotype $a_0a_3$ from other strains as well as flagella of serotypes $a_0a_2$; $a_0a_1a_2$ or $a_0a_3a_4$ mixed with flagella of serotype b as described above may be used and formulated to vaccines in an analogous manner.

EXAMPLE 3

Immunization of plasma donors with flagella vaccine 50 volontary test persons each subcutaneously received 20 myg of the vaccine produced from 5940 culture according to Example 1. After 4 weeks, 40 test persons subcutaneously received another 20 myg each, and after 4 additional weeks, immunization was once again realized with 20 myg flagellar antigen. The formation of flagellar antibodies in the course of immunization was followed in flagella ELISA as described below. After immunization, plasma from the thrice immunized test persons was collected and pooled.

Production of specific Pseudomonas aeruginosa flagella immunoglobulin preparation The isolation of the immunoglobulins containing the antibodies against Pseudomonas aeruginosa was effected according to the method described in U.S. Pat. No. 4,276,283. The pooled plasma obtained from donors was adjusted to a pH of from 7.0 to 7.2 and kept at a temperature of $-2°$ C. The solution was admixed with 8% by weight of ethanol, a precipitate substantially containing fibrinogen precipitating. After separation of this precipitate, the ethanol concentration was increased to 25% by weight and the temperature was lowered to $-6°$ C. The precipitate forming, which essentially consisted of crude immunoglobulin, was extracted in a phosphate acetate buffer and admixed with 12% by weight of ethanol at a pH of 5.3 and at $-2°$ C. The precipitate (containing alpha- and beta-globulin) was discarded and the ethanol concentration of the supernatant was increased to 25% by weight at a pH of 7.2 and a temperature of $-10°$ C., immunoglobulin thus precipitating. The pasty gamma-globulin fraction thus produced and collected was further treated according to the invention in the following manner:

1 kg of immunoglobulin paste was dissolved in 2 l of a 0.9% NaCl solution under stirring and dyalized. Thereupon, the protein concentration was adjusted to 20 g/l and the ionic strength was adjusted to 0.15. At a pH of 6.25, 176 g/l ammonium sulfate were added, the precipitate was discarded and the supernatant was admixed with ammonium sulfate until a concentration of 275 g/l was reached, the pH being adjusted to 7.2. The immunoglobulin-containing precipitate forming was dissolved in water and subjected to dialysis against tap water. Then 80 g/l polyethylene glycol were added to the solution in the presence of 150 g/l glucose at a pH of 6.0 and an ionic strength of 0.15. The precipitate was discarded, and the polyethylene glycol concentration was increased to 95 g/l at a pH of from 6.5 to 6.6. The newly formed precipitate was discarded.

Then the content of the solution of polyethylene glycol was increased to 180 g/l at a pH of 7.2, an immunoglobulin free of impurities, thus, precipitating. The product was centrifuged and the still present polyethylene glycol was eliminated by washing five times.

The intravenously administrable specific Pseudomonas flagella immunoglobulin thus obtained was reconstituted to a 5% (w/v) solution with aqua dest. The titer of antibodies specifically directed against flagella of serotype $a_0a_2$ was determined in flagella ELISA and is indicated in Table 2. The titer indicated by 1:25,000 represents the 1:25,000 dilution of the 5% immunoglobulin solution, that still showed a clearly detectable positive reaction in ELISA.

According to this method, all the other Pseudomonas aeruginosa flagella immunoglobulin preparations indicated below were produced.

To prove the efficacy of the vaccines according to the invention and of the immunoglobulin G-containing preparations active against bacterium Pseudomonas aeruginosa infections (Pseudomonas aeruginosa flagella immunoglobulin preparations) according to the invention, it is initially demonstrated that the flagellar (H) antigens (serotypes b, b($a_0$), $a_0a_2$, $a_0a_1a_2$, $a_0a_3$ and $a_0a_3a_4$, which in total contain all six partial antigens of the clinically relevant Pseudomonas pathogens, induce the formation of antibodies in man.

To this end, flagella of the above-described six relevant serotypes were separated from possibly still adhering minimal impurities on SDS polyacrylamide gel electrophoresis. The flagella bands containing the flagellin depolymerized by the detergent SDS and mercapto ethanol were obtained at the following molecular weights: type b: 53,050, type $a_0$: 52,000, type $a_0a_1a_2$: 51,250, type $a_0a_2$: 45,900, type $a_0a_3a_4$: 43,500, type $a_0a_3$: 46,700. The molecular weights were calculated via the lanes of the standard proteins carbonic anhydrase (31,000 MW), ovalbumin (45,000 MW) and BSA (66,200). The protein bands were transferred by electrotransfer from the polyacrylamide gel to a nitrocellulose foil. After free protein bindings had been blocked on the nitrocellulose foil by saturation with Tween 80, the foil was incubated in an appropriate dilution of human serum. This serum was obtained from donors who had been immunized several times with monovalent flagella vaccines containing the antigens listed above. At first, it had been made sure by ELISA controls that the sera of the donors did not contain any significant flagellar antibody titers prior to immunization.

The presence of flagella-specific antibodies after immunization was detectable by the bindings of these antibodies to the respective flagellin band on the nitrocellulose foil, which can be rendered visible on the foil by development with an enzyme-labeled second antibody and a chromogenic substrate. The staining intensity allows for limited conclusions as to the amount of specific antibody bound.

The results are summarized in Table 1. For evaluation, the staining intensities attained with the homologous antiserum are entered as "++", the bindings of the antibodies to flagellin with other serotypes being assessed in relation thereto. If no band was to be recognized on the nitrocellulose foil, "−" was entered in the Table.

TABLE 1

Cross reactions of H antisera in Western blot

| Serum against H type | Antigen on Western blot | | | | | |
|---|---|---|---|---|---|---|
| | b | b($a_0$) | $a_0a_2$ | $a_0a_1a_2$ | $a_0a_3$ | $a_0a_3a_4$ |
| b | ++ | ++ | (+) | (+) | − | (+) |
| b($a_0$) | ++ | ++ | − | − | − | − |
| $a_0a_2$ | + | + | ++ | + | + | ++ |
| $a_0a_1a_2$ | + | + | + | ++ | ++ | +++ |
| $a_0a_3$ | + | + | + | + | ++ | + |
| $a_0a_3a_4$ | + | + | + | + | + | ++ |

A cross reactivity may be taken from Table 1, because serum against a certain a-type flagellin, for instance, also reacts against other antigens of type a. Moreover, it is apparent that antibodies against a-type flagellin bind not only to the same, but even to b and b($a_0$)-type flagellins. However, the intensity of this binding usually is clearly lower than the cross reactions observed among the various a-types. On the other hand, antibodies against b and b($a_0$)-type flagellins do not or hardly bind to type-a flagellin.

To prove that the flagellar (H) antigens b, b($a_0$), $a_0a_2$, $a_0a_1a_2$, $a_0a_3$ and $a_0a_3a_4$ may be used to obtain high-titer antibodies and high-titer human immunoglobulin G-containing preparations to be administered intravenously, voluntary test persons were immunized several times at regular intervals with the monovalent antigens b, $a_0$, $a_0a_2$, $a_0a_1a_2$, $a_0a_3$ and $a_0a_3a_4$ in the course of phase I of a clinical study. Plasma was collected from these donors and pooled separately according to the serotype. From this, immunoglobulin G preparations for intravenous application were produced according to the method described in Example 3. In the following, the latter are indicated by Pseudomonas flagella immunoglobulin (PsH) supplemented by the respective flagella serotype. Thus, for instance, PsHb stands for the preparation recovered from the plasma of those donors who had been immunized with flagella vaccine from type-b antigen.

The H-serotype-specific titers were determined by flagellin ELISA. Highly purified flagella preparations were incubated in a 1% solution of sodium dodecyl sulfate for 30 min at room temperature, which resulted in the depolymerization of the flagella to flagellin monomers. Thereafter, the flagellin solution was rebuffered over a gel filtration column against carbonate buffer at a pH of 9.6 and adjusted to a concentration of 0.5 myg/ml after protein assessment. Flagellin from this solution was then bound to solid carriers (wells of a microtiter tray or comb). After blocking free protein bindings with a 0.05% solution of Tween 20 in phosphate-buffered saline, only flagella-specific antibodies were able to bind to the immobilized flagellin on the carrier.

After several washing steps, the antibodies bound were detected by an enzyme-labeled second antibody (anti-human IgG-POD conjugate) and quantitatively determined by way of colorimetry. The titers determined are indicated in Table 2 and are related to equal myg amounts of the various flagellar antigens.

The titer values indicate those dilutions of the 5% Pseudomonas flagella immunoglobulin solutions which still show clearly positive reactions in ELISA.

After hydrolysis of the protein bound to 10 ELISA combs each, the amount of immobilized protein was determined by amino acid analysis, using the amino acid compositions of the purified flagellar antigens listed in EP-A-0 252 064.

TABLE 2

ELISA titer of the immunoglobulin preparations

| H serotype | strain | titer |
|---|---|---|
| PsH-b | M-2 | 1:10,000 |
| PsH-$a_0a_2$ | 5940 | 1:25,000 |
| PsH-$a_0a_3$ | 5939 | 1:30,000 |
| PsH-$a_0a_1a_2$ | 1210 | 1:25,000 |
| PsH-$a_0a_3a_4$ | 170018 | 1:35,000 |

The next thing to demonstrate is that antibodies from the thus obtained Pseudomonas immunoglobulin preparations bind to flagellin molecules of the homologous flagellar serotype and that, moreover, the cross reactivity observed with the sera of single donors (Table 1) occurs also with hyperimmunoglobulin preparations.

As described above, Western blots of flagella preparations are produced. Instead of human sera, solutions of the five hyperimmunoglobulin preparations were used as the first antibodies; they were adjusted to equal titers in accordance with flagella ELISA and then were appropriately diluted further. Further development and evaluation of the blots took place as described in Table 1.

The results are summarized in Table 3.

TABLE 3

Cross reactivity of flagella-specific Pseudomonas immunoglobulin preparations

| AB | Antigen on Western blot | | | | | |
|---|---|---|---|---|---|---|
| | b | b($a_0$) | $a_0a_2$ | $a_0a_1a_2$ | $a_0a_3$ | $a_0a_3a_4$ |
| PsHb | ++ | ++ | (+) | (+) | (+) | + |
| PsH$a_0a_2$ | + | + | ++ | ++ | ++ | +++ |
| PsH$a_0a_1a_2$ | + | + | + | ++ | ++ | +++ |
| PsH$a_0a_3$ | + | + | ++ | ++ | ++ | ++ |
| PsH$a_0a_3a_4$ | + | + | ++ | + | + | ++ |

As already demonstrated with sera of single donors, a strong cross reactivity of all antibodies directed against a-type flagella with flagellin molecules of any a-subclass composition is observed also with the immunoglobulin preparations investigated. It is likewisely evident that (weaker) bindings of antibodies directed against a-type flagella may occur on b-type flagellin. The binding of b-type antibodies to a-type flagellin is relatively weak, yet still clearly detectable.

The activity of the antibodies according to the invention on motile Pseudomonas aeruginosa pathogens is considered to be due to the inhibition of their motility and, thus, of the propagation of the focus of infection.

The inhibition of motility may be demonstrated on soft-agar swarm trays. A filter paper round was soaked with 20 myl of a 0.5% solution of PsH in HBSSG. It was placed on an inoculum of 10h5 pathogens in 10 myl after the pathogen suspension had penetrated into the soft agar. The degree of the inhibition of motility was determined by way of a control applied on the same tray, in which case a filter paper round soaked with Hank's Balanced Salt Solution with gelatine (HBSSG)

had been placed on the inoculum. Like in Western blot, cross reactions between antibodies against various a-serotype flagella and all of the pathogens investigated, and flagella of various a-subtype compositions were to be noted. Even the cross reaction between a-type antibodies and b-flagella observed in the Western blot could be observed. The cross reaction between b-type antibodies and a-type flagella of all subclasses was more distinct than in the Western blot.

The results are summarized in Table 4, the diameters of the swarm zones of pathogens incubated with antibodies being compared to controls free of antibodies being on the same tray: "++" serves to denote a swarm zone diameter smaller than that of the control by at least 40%; "+" denotes a diameter smaller than that of the control by at least 20%, but by 40% at the most.

TABLE 4

| Cross reactions of H antibodies in motility inhibition test | | | | | | |
|---|---|---|---|---|---|---|
| AB against | H antigen of pathogen on swarm tray | | | | | |
| H type | b | b($a_0$) | $a_0a_1a_2$ | $a_0a_2$ | $a_0a_3$ | $a_0a_3a_4$ |
| b | ++ | ++ | ++ | + | + | ++ |
| $a_0a_1a_2$ | + | + | + | + | + | + |
| $a_0a_2$ | + | + | ++ | ++ | ++ | + |
| $a_0a_3$ | + | + | + | ++ | ++ | ++ |
| $a_0a_3a_4$ | ++ | + | + | ++ | + | ++ |

The results of Table 4 demonstrate that the antibodies according to the invention obtained with flagellar (H) antigens inhibit the motility of Pseudomonas bacterial strains.

By the inhibition of the motility of the bacteria present in a focus, their further propagation after colonization in the patient's body is prevented, yet the bacteria present in the focus retain their capability of stressing the patient's organism by releasing, e.g., toxins, proteases, etc. Proper protection against infections, therefore, is guaranteed only if the antibodies formed upon active immunization induce the rapid killing of the invader bacteria.

In the following, evidence is furnished that flagellar (H) antibodies induce phagocytosis and intracellular killing of the homologous Pseudomonas bacterial strain.

To carry out the phagocytosis experiments, pathogens of the strains M-2 (b), WR-5 ($a_0a_2$), 1210 ($a_0a_1a_2$), 5939 ($a_0a_3$) and 170018 ($a_0a_3a_4$) were grown in Luria Broth Medium and were diluted to a number of live pathogens of 8.10h8 pathogens per ml just before the beginning of the stationary growth phase in HBSSG. Of all the 5% flagella immunoglobulin preparations, 1:18, 1:72 and 1:288 dilutions in HBSSG were prepared. 450 myl each, of these dilutions were incubated with 50 myl pathogen suspension and 4.5 ml HBSSG for 2 h on ice. During this incubation, binding of the specific antibodies to bacterial cells occurred.

Human granulocytes are used as the phagocyting cells. They were obtained from freshly isolated buffy coats. The buffy coats were freed from the major portion of erythrocytes by underletting saline dextrose dextrane solution. Several centrifugation steps followed, by which the remaining erythrocytes and thrombocytes were largely removed. After washing in saline, the number of cells was determined in the Coulter counter and adjusted to 1.10h7 cells/ml in HBSSG. A differential blood count was taken from this cell suspension. The ratio of granulocytes to lymphocytes was to be in the standard range of about 6:4. The content of monocytes usually ranges between 4 and 8%. Cell isolates that comply with these criteria may be used in the phagocytosis test.

Absorbed human serum (ABA) from a pool of donors of blood type AB was used as the complement source. Before that, the serum was adsorbed on all the pathogens mentioned above, 1 ml serum per pathogen being incubated on ice with 5×10h9 pathogens for 0.5 hours. Each incubation was followed by a centrifugation step of 5 min at 8,000 g. After the final incubation, it was additionally centrifuged for 15 min at 14,000 g. After absorption, the complement content of the serum in C'H50 units was assayed. It was by 15% lower than that of the starting serum. The ABA serum thus obtained was prediluted to 1:50 in Hank's buffer and used in the phagocytosis test.

To the phagocytosis test mixture, 100 myl of the granulocyte suspension, 60 myl of the pathogen suspension and 40 myl of the absorbed AB serum were mixed in the well of a microtiter tray. Immediately upon mixing, and after 1 h of incubation at 37° C., 25 myl were taken from the test mixture and diluted in 5 ml bidist. water. In doing so, the granulocytes were osmotically lysed, liberating bacterial cells contained therein. 25 myl of this suspension were plated out to determine the number of live pathogens. Based on the colony numbers of the 0 and 60 min-values, the killing rate was calculated according to the following formula:

$$\% \text{ killing} = 1 - \frac{\frac{\text{Number } t = 60}{\text{control}}}{\text{number } t = 0} \times 100$$

The calculation of the control value was based on the t=0 and t=60 min live pathogen values that had been obtained in the test from a position at which unloaded pathogens had been used instead of those loaded with antibodies. The quotient from the thus obtained 60 and 0 min-values was substituted in the above formula as a control.

The results of the phagocytosis tests are summarized in Table 5.

TABLE 5

| Killing of Pseudomonas aeruginosa after opsonization with flagellar antibodies by human granulocytes | | | | | |
|---|---|---|---|---|---|
| AB against | H antigen of pathogen in phagocytosis test | | | | |
| H type | b | $a_0a_1a_2$ | $a_0a_2$ | $a_0a_3$ | $a_0a_3a_4$ |
| PsHb | 1:30 | high* | high | 40 | 27 |
| PsH$a_0a_2$ | 1:60 | 102 | 120 | 86 | 65 |
| PsH$a_0a_3$ | 1:78 | 105 | high | 108 | 84 |
| PsH$a_0a_1a_2$ | 1:60 | 200 | high | 125 | 72 |
| PsH$a_0a_3a_4$ | 1:78 | high | 190 | 80 | 78 |

*Less than 50% of the pathogens used were killed with all antibody concentrations The titer values indicated in the Table reveal that concentration of the H-type specific flagella immunoglobulin preparation which had to be adjusted for the opsonization of 4×10h8 pathogens in a 5 ml mixture in order to reach a killing rate of 50% of the pathogens used in the phagocytosis test. These phagocytosis titers were calculated as the quotient from the absolute values of the homologous antibody titers established in flagella ELISA and from the dilution factors determined in phagocytosis assay at which 50% of the pathogens used was killed by the respective (homologous or heterologous) flagella immunoglobulin.

From Table 5, it is apparent that Pseudomonas flagella immunoglobulin preparations opsonize pathogens with homologous and heterologous flagellar serotypes. What is particularly striking is the cross reaction of all the PsHa preparations with any a-type and b-type pathogen. Particularly low concentrations of PsHa$_{0a2}$ induce the phagocytosis of pathogens with a-type and b-type flagella. To kill b-type pathogens, higher concentrations of PsHa than of PsHb preparations are required.

These results demonstrate that antibodies with a$_{0a2}$ specificity exhibit a protective action against pathogens with all clinically relevant flagellar serotypes, and that this protective action must be intensified in respect of pathogens with b-type flagella in a mixture consisting of a$_{0a2}$-antibodies and b-antibodies.

It has not been known so far whether antibodies isolated from plasma of donors immunized with highly purified flagellar antigens possess protective action against *Pseudomonas aeruginosa* infections. By the phagocytosis test described above, this proof was furnished for PsH preparations having a specificity for all clinically relevant H-serotypes.

In the following Table 6, the efficacy of the monovalent antibody preparation PsHa$_{0a2}$ of the invention and the activities of the bivalent preparations PsHb/a$_{0a2}$, PsHb/a$_{0a1a2}$, PsHb/a$_{0a3}$ and PsHb/a$_{0a3a4}$ of the invention, which were produced according to the method described in Example 2, are indicated.

TABLE 6

Efficacy of therapeutic Pseudomonas immunoglobulin preparations in phagocytosis test

| AB against H type | H-antigen of pathogen in phagocytosis test | | | | | |
|---|---|---|---|---|---|---|
| | b | a$_{0a1a2}$ | a$_{0a2}$ | a$_{0a3}$ | a$_{0a3a4}$ | 0 |
| PsHa$_{0a2}$ | 1:60 | 102 | 120 | 86 | 65 | 87 |
| Standard | 1:3 | 19 | 31 | 28 | 9 | 18 |
| PsHb/a$_{0a2}$ | 1:6 | 24 | 30 | 80 | 20 | 32 |
| PsHb/a$_{0a1a2}$ | 1:5 | 28 | 59 | 32 | 13 | 27 |
| PsHb/a$_{0a3}$ | 1:11 | 23 | 32 | 25 | 7 | 20 |
| PsHb/a$_{0a3a4}$ | 1:19 | 34 | 15 | 54 | 6 | 26 |

In Table 6, the efficacy of the preparation PsHa$_{0a2}$ in the phagocytosis test is indicated at first. The titer data represent those immunoglobulin concentrations which have to be adjusted when loading the pathogens in order to reach a 50% killing of the pathogens in the subsequent phagocytosis test. FIG. 1 illustrates how these titers have been established: 450 myl of 1:18, 1:72 and 1:288 pre-dilutions of the 5% PsHa$_{0a2}$ solution are mixed with 50 myl of a suspension of 8×10h8 5940 pathogens/ml and with 4.5 ml Hank's buffer with gelatin. Hence follow final dilutions of 1:200, 1:800 and 1:3,200. The titer of PsHa$_{0a2}$ determined in flagella ELISA is 1:25,000. Thus, the concentrations of the flagellar antibodies during loading of the bacteria are evaluated at 1:125, 1:31.3 and 1:7.8. In FIG. 1, the pathogen killing rate (extinction) attained in the phagocytosis test is plotted against these immunoglobulin concentrations. From these killing curves, the concentrations of immunoglobulin indicated in the Table at which 50% of the pathogens investigated are killed, can be established.

In order to be able to estimate the efficacy of the PsHa$_{0a2}$ preparation, a standard representing a mixture of all five PsH preparations listed in Table 6 serves as a control, all individual components having been adjusted to an ELISA titer of 1:2,000.

Moreover, Table 6 reveals the efficacy of mixtures of PsHb with the preparations PsHa$_{0a2}$, PsHa$_{0a1a2}$, PsHa$_{0a3}$ and PsHa$_{0a3a4}$, respectively. These mixtures were adjusted to an anti-b titer of about 1:7,500 and to a homologous anti-a titer of the same extent. Table 6 indicates the phagocytosis titers that have been established with these immunoglobulin mixtures for *Pseudomonas aeruginosa* strains with flagella epitopes of all clinically relevant serotypes.

These titers represent that immunoglobulin mixture concentration which, based on a titer of 1:7,500, had to be adjusted for both components when loading the pathogens in order to attain 50% killing of the pathogens used in the subsequent phagocytosis test.

From FIG. 2, it can be taken how these titers have been established for the mixture of PsHb and PsHa$_{0a3}$: A mixture of 1 ml PsHb and 0.33 ml PsHa$_{0a3}$, resulting in a b- and a$_{0a3}$ titer of 1:7,500, was further diluted as described above and used in the phagocytosis test. In FIG. 2, the killing rate achieved in the phagocytosis test has been plotted against the antibody titers for the individual components b and a$_{0a3}$ present when loading the bacteria.

Table 6 demonstrates that the PaHa$_{0a2}$ preparation is active against all relevant serotypes, yet its efficacy is not as pronounced as that of the standard. In contrast, mixtures consisting of PsHb and one of the preparations PsHa$_{0a2}$, PsHa$_{0a1a2}$, PsHa$_{0a3}$ or PsHa$_{0a3a4}$ have efficacies almost equal to that of the standard preparation, clearly exceeding the efficacies of the individual component preparations (cf. Table 5). To illustrate this fact, average titers for the various preparations and mixtures are indicated in the column under 0.

Immunoglobulin preparations obtained by mixing from plasma of donors who had been immunized with flagellar antigen of serotype b and one of the four a-subtype combinations examined hence are capable of inducing the killing of pathogens with flagella of all clinically relevant serotypes. In accordance with the above results, also bivalent vaccines according to the invention, which consist of the flagellar antigen b and one of the antigens a$_{0a2}$, a$_{0a1a2}$, a$_{0a3}$ or a$_{0a3a4}$, or an immunoglobulin preparation according to the invention obtained after application thereof, naturally, are able to protect against infections with flagella-bearing *Pseudomonas aeruginosa* bacteria.

The direct proof of the protective action of antigens to be used for active immunization is feasible only in the animal model and will be explained in the following.

In order to simulate the situations predisposing patents to Pseudomonas infections, two animal models described in the literature were used: the burned mouse model (Stieritz, D. D. and I. A. Holder (1975) J. Infect. Dis. 131, 688–691) and the Endoxan model (Cryz, S. J. Jr., Fürer, E., Germanier, R. (1983), Infect. Immunity 40, 659–664).

For both models, the LD50 dose of *Pseudomonas aeruginosa* in non-immunized animals was determined, which, in the case of the Endoxan model, were immunosuppressed; in the burned mouse model a burn of a defined size was set. After immunization with the flagellar (H) antigens listed in Table 7, burned animals and immunosuppressed animals were infected with a multiple of the previously determined LD50 pathogen number of the homologous Pseudomonas strain. Table 7 shows the multiples of the LD50 pathogen numbers that are tolerated by 100% of the animals immunized with the concentration of antigen indicated in the Endoxan and in the burned mouse models. The results document the efficacy of a bivalent flagella vaccine in the normal and in the immunosuppressed animals.

TABLE 7

Active protection assay with *Pseudomonas aeruginosa* flagella vaccine

| Antigen | Amount/mouse with Al(OH)$_3$ as adjuvant | Immunization days before challenge | Endoxan model protective factor (x LD50) | | Burned mouse model protective factor (x LD50) | |
|---|---|---|---|---|---|---|
| b | 3 myg | 14 | b | $3 \times 10^1$ | $>10^4$ | |
| $a_0a_3$ | 1,5 myg | 14 | $a_0a_3$ | $2 \times 10^1$ | $10^3$ | |
| b/$a_0a_3$ | 3/1,5 myg | 14 | b | $10^2$ | $>10^4$ | b |
| | | | $a_0a_2$ | $4 \times 10^1$ | $10^3$ | $a_0a_1a_2$ |
| | | | $a_0a_1a_2$ | $2 \times 10^1$ | $10^4$ | $a_0a_2$ |
| | | | $a_0a_3$ | $10^2$ | $10^4$ | $a_0a_3$ |
| | | | $a_0a_3a_4$ | $10^2$ | $>10^4$ | $a_0a_3a_4$ |

What we claim is:

1. A vaccine active against *Pseudomonas aeruginosa* infections, wherein said vaccine has a single flagellar (H) antigen of serotype a and a flagellar (H) antigen of serotype b, wherein said flagellar antigen of serotype a has a serotype selected from the group consisting of $a_0a_2$, $a_0a_3$, $a_0a_1a_2$, and $a_0a_3a_4$.

2. A vaccine as set forth in claim 1, wherein the flagellar (H) antigen of serotype a has serotype $a_0a_2$, which $a_0a_2$ antigen consists of monomeric components and contains the amino acids: aspartic acid, threonine, serine, glutamic acid, glycine, alanine, valine, isoleucine, leucine, tyrosine, phenylalanine, lysine and arginine at a ration of 68:41:37:46:44:73:29:29:37:3:10:16:16, having a molecular weight of 45,900.

3. A vaccine as set forth in claim 1, wherein the flagellar (H) antigen of serotype a has serotype $a_0a_1a_2$, which $a_0a_1a_2$ antigen consists of monomeric components and contains the amino acids: aspartic acid, threonine, serine, glutamic acid, glycine, alanine, valine, isoleucine, leucine, tyrosine, phenylalanine, lysine and arginine at a ration of 76:44:40:52:40:81:32:32:41:4:12:20:18, having a molecular weight of 51,250.

4. A vaccine as set forth in claim 1, wherein the flagellar (H) antigen of serotype a has serotype $a_0a_3$, which $a_0a_3$ antigen consists of monomeric components and contains the amino acids: aspartic acid, threonine, serine, glutamic acid, glycine, alanine, valine, isoleucine, leucine, tyrosine, phenylalanine, lysine and arginine at a ration of 69:35:38:44:47:73:30:30:60:3:12:21:16, having a molecular weight of 46,700.

5. A vaccine as set forth in claim 1, wherein the flagellar (H) antigen of serotype a has serotype $a_0a_3a_4$, which $a_0a_3a_4$ antigen consists of monomeric components and contains the amino acids: aspartic acid, threonine, serine, glutamic acid, glycine, alanine, valine, isoleucine, leucine, tyrosine, phenylalanine, lysine and arginine at a ration of 64:33:35:42:44:68:29:29:37:3:10:19:15, having a molecular weight of 43,500.

6. A vaccine as set forth in claim 2, wherein the flagellar (H) antigen of serotype b consists of monomeric components and contains the amino acids: aspartic acid, threonine, serine, glutamic acid, glycine, alanine, valine, isoleucine, leucine, tyrosine, phenylalanine, lysine and arginine at a ration of 74:48:48:49:51:91:38:30:43:4:13:18:18, and having a molecular weight of 53,050.

7. A method of producing a vaccine active against *Pseudomonas aeruginosa* infections and having an efficacy directed against any combination of flagellar (H) serotype determinants $a_0$, $a_1$, $a_2$, $a_3$, $a_4$, and b, which vaccine has an antigen that consists of a single flagellar (H) antigen of serotype a and a single flagellar (H) antigen of serotype b, comprising the steps of (1) separately obtaining a single flagellar (H) antigen of serotype a and a flagellar (H) antigen of serotype b from *Pseudomonas aeruginosa* cultures, (2) purifying and sterile-filtering said serotype a and serotype b antigens, (3) formulating said antigens into separate galenic preparations and (4) combining said galenic preparations into one preparation.

8. A method as set forth in claim 7, comprising mixing the flagellar (H) antigen with an adjuvant.

9. A method as set forth in claim 8, wherein said adjuvant is Al(OH)$_3$.

10. A method as set forth in claim 7 comprising mixing the flagellar (H) antigen with a preservant.

11. A method as set forth in claim 10, wherein said preservant is merthiolate.

12. A vaccine as set forth in claim 3 wherein, the flagellar (H) antigen of serotype b consists of monomeric components and contains the amino acids: aspartic acid, threonine, serine, glutamic acid, glycine, alanine, valine, isoleucine, leucine, tyrosine, phenylalanine, lysine and arginine at a ratio of 74:48:48:49:51:91:38:30:43:4:13:18:18, having a molecular weight of 53,050.

13. A vaccine as set forth in claim 4 wherein the flagellar (H) antigen of serotype b consists of monomeric components and contains the amino acids: aspartic acid, threonine, serine, glutamic acid, glycine, alanine, valine, isoleucine, leucine, tyrosine, phenylalanine, lysine and arginine at a ratio of 74:48:48:49:51:91:38:30:43:4:13:18:18, having a molecular weight of 53,050.

14. A vaccine as set forth in claim 5 wherein the flagellar (H) antigen of serotype b consists of monomeric components and contains the amino acids: aspartic acid, threonine, serine, glutamic acid, glycine, alanine, valine, isoleucine, leucine, tyrosine, phenylalanine, lysine and arginine at a ratio of 74:48:48:49:51:91:38:30:43:4:13:18:18, having a molecular weight of 53,050.

15. A method of inhibiting the motility of all clinically relevant strains of *Pseudomonas aeruginosa*, comprising administering the vaccine as set forth in claim 1 to a patient.

* * * * *